United States Patent [19]

Meek et al.

[11] Plant 4,585

[45] Jul. 29, 1980

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 18,484

[22] Filed: Mar. 8, 1979

[51] Int. Cl.[2] ..... A01H 5/00

[52] U.S. Cl. ..... Plt./77

[58] Field of Search ..... Plt./77

*Primary Examiner*—Robert E. Bagwill

*Attorney, Agent, or Firm*—Donald D. Jeffery

[57] ABSTRACT

A chrysanthemum plant known by the cultivar name Surf and particularly characterized as to uniqueness by the combined characteristics of flat capitulum form; decorative capitulum type; white ray floret color; diameter across face of capitulum ranging from 65 to 95 mm. at maturity; uniform eight week photoperiodic flowering response to short days; short plant height when grown as a pinched spray pot, and semi-spreading branching pattern.

1 Drawing Figure

The present invention comprises a new and distinct cultivar of *Chrysanthemum morifolium,* Ramat., hereinafter referred to by the cultivar name Surf.

Surf is a product of a planned breeding program which had the objective of creating new chrysanthemum cultivars with decorative capitulum type, with yellow or white ray floret color, with eight or nine week flowering response, and with the ability to produce commercially acceptable quality in year round spray pot mum programs. Such traits in combination were not present in previously available commercial cultivars.

Surf was originated from a cross made in a controlled breeding program in Barberton, Ohio in 1977. The female parent was Spirit, disclosed in U.S. Plant Pat. No. 3,813, a white spider. The male parent of Surf was #75179131 (unnamed seedling), a yellow single spoon originated by the present inventors from a cross between #73116030 (unnamed seedling) and #71388001 (unnamed seedling). #73116030 and #71388001 are products of the present inventors.

Surf was discovered and selected as one flowering plant within the progeny of the stated cross by Jack M. Meek and William E. Duffett on Aug. 30, 1977 in a controlled environment in Salinas, Calif.

The first act of asexual reproduction of Surf was accomplished when vegetative cuttings were taken from the initial selection in January, 1978 in a controlled environment in Salinas, Calif., by a technician working under formulations established and supervised by Jack M. Meek and William E. Duffett. Continued asexual reproduction by vegetative cuttings for evaluative tests in flowering and stock programs in conjunction with horticultural examination of selected units initiated May 3, 1978 has demonstrated that the combination of characteristics as herein disclosed for Surf are firmly fixed and are retained through successive generations of asexual reproduction.

Surf has not been observed under all possible environmental conditions. The phenotype may vary significantly with variations in environment such as temperature, light intensity, and daylength. The following observations, measurements, and comparisons describe plants grown in Salinas, Calif. under greenhouse conditions which approximate those generally used in commercial practice. The following traits have been repeatedly observed and are determined to be basic characteristics of Surf which in combination distinguish this chrysanthemum as a new and distinct cultivar:

(1) Flat capitulum form.

(2) Decorative capitulum type.

(3) White ray floret color.

(4) Diameter across face of capitulum ranging from 65 to 95 mm. at maturity.

(5) Uniform eight week photoperiodic flowering response to short days.

(6) Short plant height (requiring 2–3 long day weeks prior to pinch and short days and 1 application 2500 ppm B-9 SP 14 to 21 days after the beginning of short days to attain a flowered plant height of 30 to 35 cm.).

(7) Semi-spreading branching pattern.

The accompanying photographic drawings show typical inflorescence and foliage characteristics of Surf, with colors being as nearly true as possible with illustrations of this type. Sheet 1 is a color photograph of a specimen plant of Surf. Sheet 2 is a black and white photograph showing three views of the capitulum of Surf. Sheet 3 is a black and white photograph of the foliage of Surf at three stages of growth.

Of the many commercial cultivars known to the present inventors, the most similar in comparison to Surf are the parental cultivar, Spirit, and the cultivar Paragon, disclosed in U.S. Plant Pat. No. 3,368. Reference is made to attached Chart A which compares certain characteristics of Surf to those same characteristics of Spirit and Paragon. General comparisons are as follows:

(1) In comparison to Spirit, Surf has different capitulum type, smaller diameter across face of capitulum, more spreading branching pattern, shorter plant height, and faster flowering response period. The capitulum form and ray floret color of Surf are similar to those same characteristics of Spirit.

(2) In comparison to Paragon, Surf has smaller diameter across face to capitulum, shorter plant height and faster flowering response period. The capitulum form capitulum type, ray floret color, and branching pattern of Surf are similar to those same characteristics of Paragon.

In the following description color references are made to A Limit Color Cascade by the Munsell Company, 1972 edition. The color values were determined between 2:00 and 2:30 p.m. on Jan. 30, 1979 under 50 foot-candle light intensity at Salinas, Calif.

Classification:

*Botanical.*—*Chrysanthemum morifolium,* Ramat., cv Surf.

*Commercial.*—Decorative spray pot mum.

I. INFLORESCENCE

A. Capitulum:

*Form.*—Flat.

*Type.*—Decorative.

*Diameter across face.*—65 to 95 mm.

B. Corolla of ray florets (See Sheets 1 and 2):

*Color (abaxial).*—23-1 (immature) to white (mature).

*Color (adaxial).*—White.

C. Reproductive organs

*Gynoecium.*—Present in both ray and disc florets.

*Androecium.*—Present in disc florets only; scant pollen.

II. Plant

A. General appearance

*Height.*—Short, requiring 2–3 long day weeks prior to pinch and short days and 1 application 2500 ppm B-9 SP 14 to 21 days after pinch to attain height as a flowered plant of 30 to 35 cm.

*Branching pattern.*—Semi-spreading.

B. Foliage (See Sheets 1 and 3):

*Color (abaxial).*—Approximately 20-15.

*Color (adaxial).*—20-14 overlaid with white.

Chart A

Comparison of Surf, Spirit and Paragon.

| Cultivar | Ray Floret Color | Capitulum Form and Type | Branching Pattern | Diameter Across Face of Capitulum | Plant Height | Flowering Response Period |
|---|---|---|---|---|---|---|
| Surf | White | Flat decorative | Semi-spreading | 65 to 95 mm. | Short | 8 week |
| Spirit | White | Flat decorative | Semi-upright | 75 to 115 mm. | Medium | 9 week |
| Paragon | White | Flat decorative | Semi-spreading | 115 to 140 mm. | Medium | 9 week |

Comparisons made of plants grown as pinched spray pots in Salinas, California.

We claim:

1. A new and distinct cultivar of *Chrysanthemum morifolium,* Ramat., plant as shown and described, known by the cultivar name Surf and particularly characterized as to uniqueness by the combined characteristics of flat capitulum form; decorative capitulum type; white ray floret color; diameter across face of capitulum ranging from 65 to 95 mm. at maturity; uniform eight week flowering response; short plant height, and semi-spreading branching pattern.

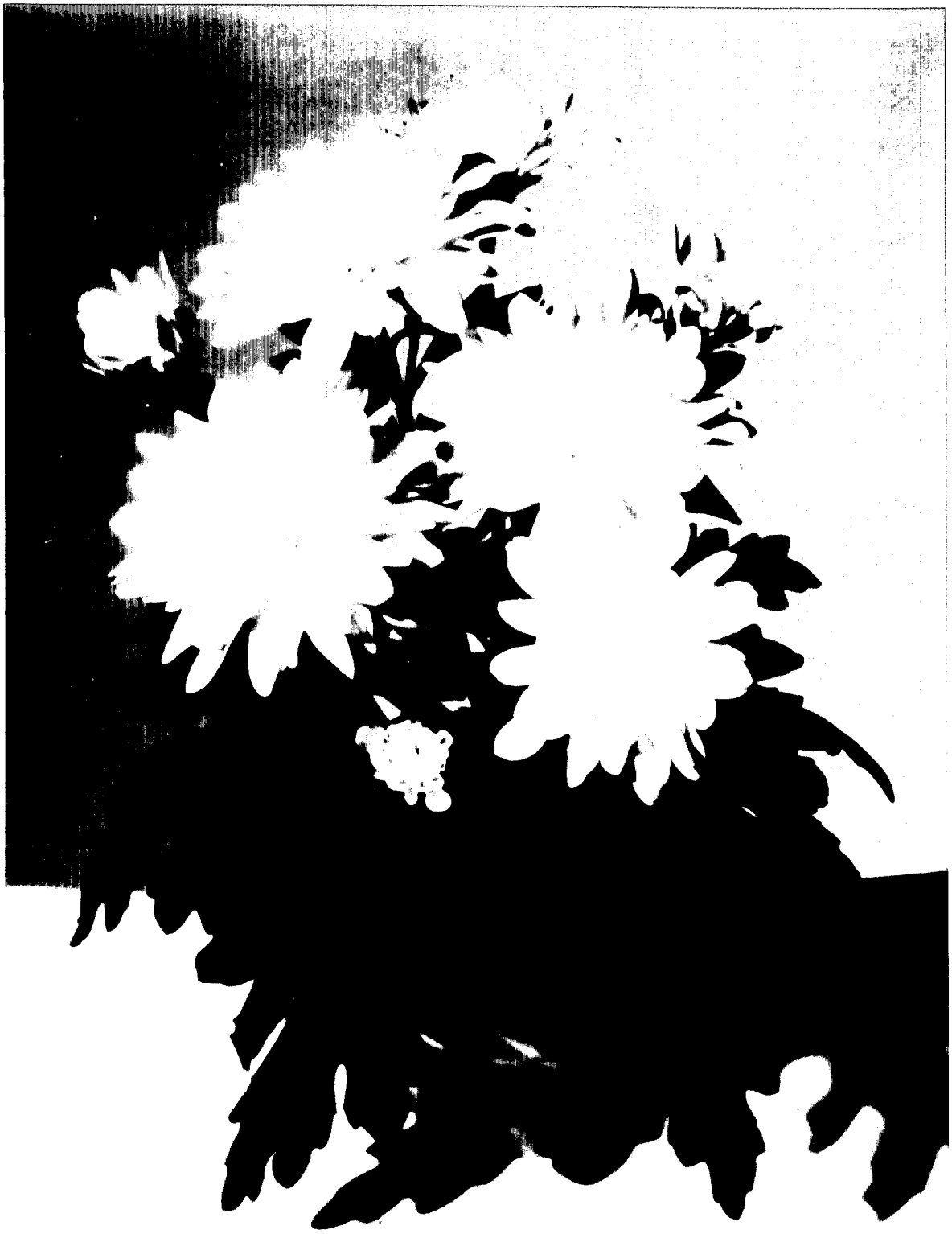

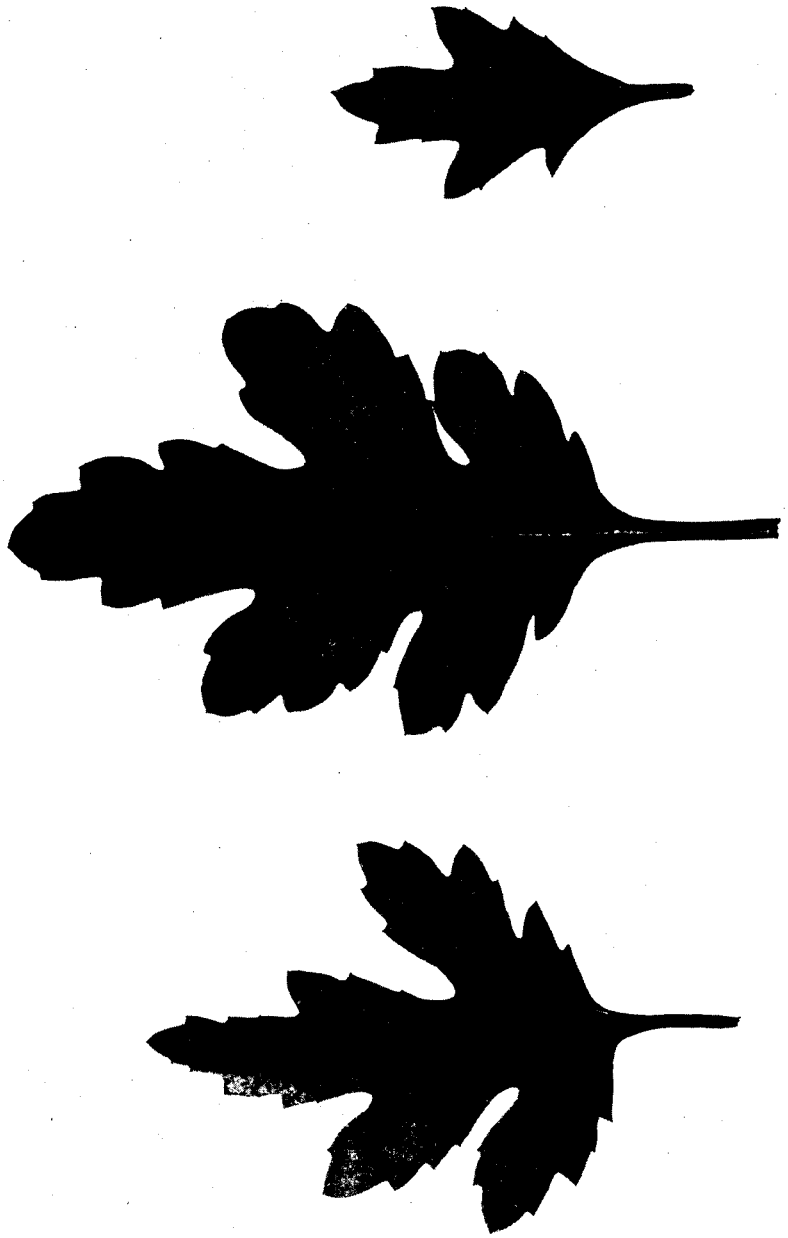

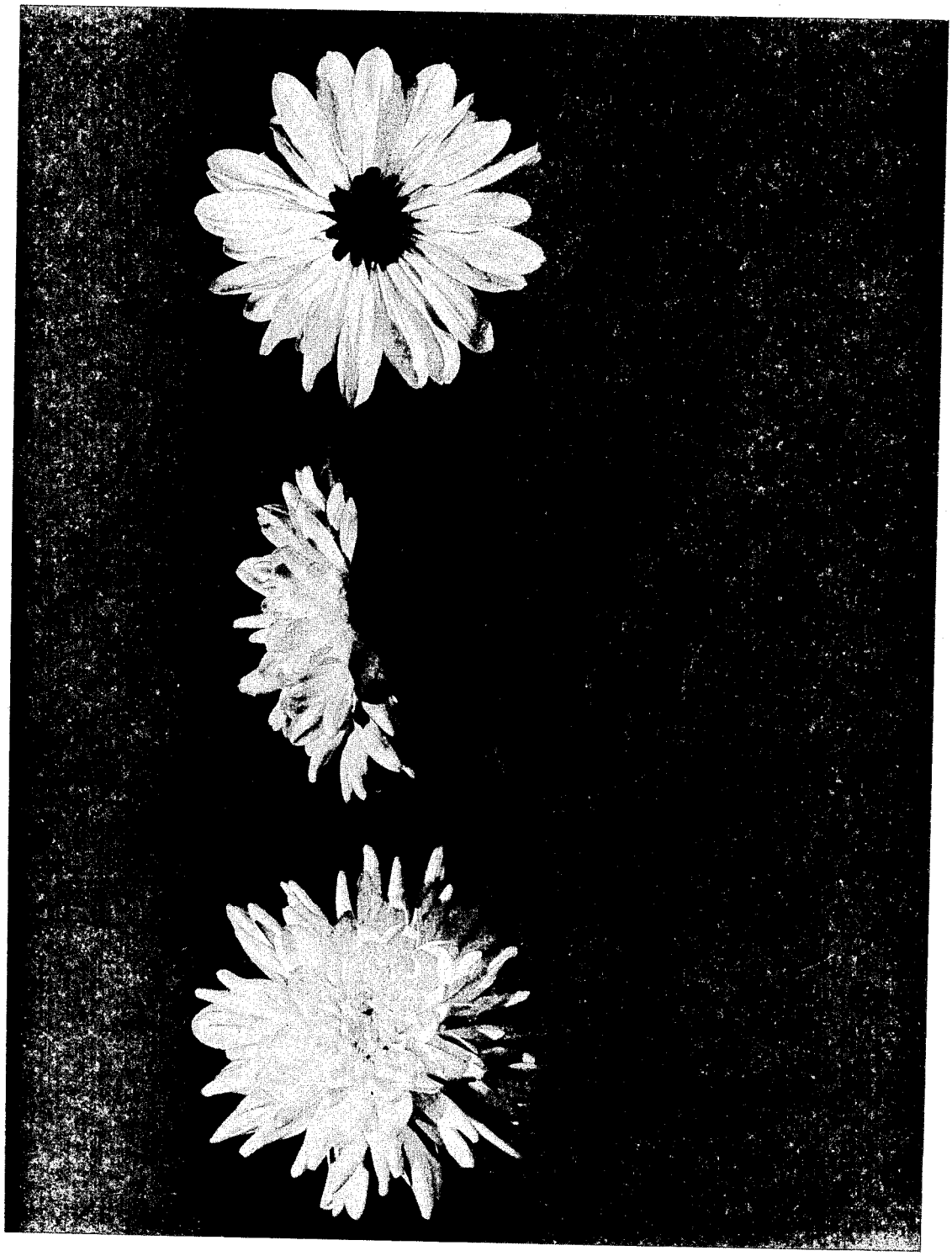

* * * * *